(12) United States Patent
Cheng et al.

(10) Patent No.: US 8,211,115 B2
(45) Date of Patent: Jul. 3, 2012

(54) VARIABLE SIZE RETRIEVAL BASKET

(75) Inventors: Eric Cheng, Bloomington, IN (US); James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1127 days.

(21) Appl. No.: 11/122,326

(22) Filed: May 5, 2005

(65) Prior Publication Data

US 2005/0261706 A1 Nov. 24, 2005

Related U.S. Application Data

(60) Provisional application No. 60/568,272, filed on May 6, 2004.

(51) Int. Cl.
*A61B 17/24* (2006.01)
*A61B 17/26* (2006.01)
*A61M 29/00* (2006.01)

(52) U.S. Cl. .......... 606/114; 606/127; 606/200

(58) Field of Classification Search ........... 606/113, 606/114, 108, 127, 128, 191, 200, 110–112, 606/115; 604/265
See application file for complete search history.

(56) References Cited

U.S. PATENT DOCUMENTS

| | | | | |
|---|---|---|---|---|
| 5,728,067 A * | 3/1998 | Enger | | 604/103.04 |
| 5,919,570 A * | 7/1999 | Hostettler et al. | | 428/424.8 |
| 6,099,534 A * | 8/2000 | Bates et al. | | 606/127 |
| 6,159,220 A * | 12/2000 | Gobron et al. | | 606/127 |
| 6,350,266 B1 * | 2/2002 | White et al. | | 606/114 |
| 6,575,995 B1 * | 6/2003 | Huter et al. | | 606/200 |
| 6,656,517 B2 * | 12/2003 | Michal et al. | | 427/2.24 |
| 6,695,834 B2 * | 2/2004 | Gellman et al. | | 606/2.5 |
| 6,780,193 B2 | 8/2004 | Leslie et al. | | |
| 7,087,062 B2 * | 8/2006 | Dhindsa | | 606/127 |
| 7,101,380 B2 * | 9/2006 | Khachin et al. | | 606/127 |
| 2002/0068944 A1 | 6/2002 | White et al. | | |
| 2003/0018355 A1 * | 1/2003 | Goto et al. | | 606/200 |
| 2003/0050663 A1 * | 3/2003 | Khachin et al. | | 606/200 |
| 2003/0204202 A1 | 10/2003 | Palmer et al. | | |
| 2004/0097964 A1 | 5/2004 | Dhindsa | | |
| 2004/0260331 A1 * | 12/2004 | D'Aquanni et al. | | 606/200 |
| 2005/0119668 A1 * | 6/2005 | Teague et al. | | 606/127 |

FOREIGN PATENT DOCUMENTS

| | | |
|---|---|---|
| EP | 1 273 268 A1 | 1/2003 |
| WO | WO 00/71036 A2 | 11/2000 |
| WO | WO 2004/032769 A1 | 4/2004 |

OTHER PUBLICATIONS

Written Opinion of the International Searching Authority issued in International Application No. PCT/US2005/015730, dated Sep. 26, 2005.
International Search Report issued in International Application No. PCT/US2005/015730, dated Sep. 26, 2005.

* cited by examiner

*Primary Examiner* — Kathleen Sonnett
*Assistant Examiner* — Jocelin Tanner
(74) *Attorney, Agent, or Firm* — Finnegan, Henderson, Farabow, Garrett & Dunner, LLP

(57) ABSTRACT

A medical device includes an elongate member defining a lumen and a tipless basket having a proximal end and a distal end. The basket is retractable within and extendable from the lumen. The basket includes a plurality of proximal legs extending from the proximal end of the basket and a plurality of distal legs extending to the distal end of the basket. Each of the plurality of proximal legs is connected to an end of at least two of the plurality of distal legs between the proximal and distal ends of the basket.

35 Claims, 1 Drawing Sheet

VARIABLE SIZE RETRIEVAL BASKET

PRIORITY DATA

This application claims the benefit of U.S. Provisional Patent Application No. 60/568,272 filed May 6, 2004.

FIELD OF THE INVENTION

This disclosure relates generally to medical devices and more particularly to stone retrieval devices.

BACKGROUND OF THE INVENTION

Extractors have been used for the removal of stones or calculi from within the body. One type of extractor has a sheath and includes a basket at its distal end. The basket may have a number of legs, and may be collapsed within the sheath to achieve a reduced diameter profile. The basket may also be opened when it extends beyond the sheath. Once opened, a targeted stone may be captured within the basket.

The baskets of some extractors may have only one configuration when extending beyond the sheath, regardless of the size of the targeted stone. For example, a basket having four legs may maintain its four leg configuration, and may maintain substantially the same spacing between each leg, whether capturing small stones or large stones. Such extractors may make it more difficult to capture stones of varying sizes and may hinder the user's ability to reduce the size of some stones through, for example, laser lithotripsy.

The present disclosure provides stone retrieval devices and methods of using the same that avoid some or all of the aforementioned shortcomings of existing devices.

SUMMARY OF THE INVENTION

In accordance with an exemplary embodiment of the present disclosure, a medical device includes an elongate member defining a lumen and a tipless basket having a proximal end and a distal end. The basket is retractable within and extendable from the lumen. The basket includes a plurality of proximal legs extending from the proximal end of the basket and a plurality of separate distal legs extending to the distal end of the basket. Each of the plurality of proximal legs is connected to an end of at least two of the plurality of separate distal legs between the proximal and distal ends of the basket.

In addition, the plurality of proximal legs may be formed from a single piece of material and the elongate member may comprise a metal coated with a polymer. The basket may have a partially expanded position in which at least a portion of the plurality of proximal legs is disposed within the lumen of the elongate member, and a midsection of each of the plurality of separate distal legs extends distal each end of each of the plurality of separate distal legs. Each leg of the plurality of separate distal legs may extend between distal ends of two legs of the plurality of proximal legs and the basket may have a substantially circular shape in an expanded position. Moreover, at least one leg of the plurality of separate distal legs may extend in a direction substantially perpendicular to a longitudinal axis of the basket when the basket is in an expanded position. A portion of at least one leg of the plurality of separate distal legs may be coated with a protective material.

In another exemplary embodiment of the present disclosure, a medical device includes an elongate member defining a lumen and a basket retractable within and extendable from the lumen. The basket includes a plurality of proximal legs extending from a proximal end of the basket and a plurality of separate distal legs extending to a distal end of the basket. Each of the plurality of proximal legs is connected to an end of at least two of the plurality of separate distal legs between the proximal and distal ends of the basket. The plurality of separate distal legs include a plurality of first legs and a plurality of second legs. Each leg of the plurality of first legs are formed from a same piece of material as a corresponding leg of the plurality of second legs.

In embodiments the basket may further include an atraumatic tip connecting the plurality of first legs with the plurality of second legs. The atraumatic tip may be a knot formed by tying the plurality of first legs to the plurality of second legs. A portion of at least one leg of the plurality of first and second legs may be coated with a protective material. The basket may have a partially expanded position in which at least a portion of the plurality of proximal legs is disposed within the lumen of the elongate member, and a distal end of each of the plurality of first legs extends distal a proximal end of each of the plurality of first legs. The basket may have a substantially circular shape in an expanded position. In addition, at least one leg of the plurality of first and second legs may extend in a direction substantially perpendicular to a longitudinal axis of the basket when the basket is in an expanded position. In addition, the proximal ends of the plurality of first legs may be connected, the proximal ends of the plurality of second legs may be connected, and the proximal ends of the plurality of first legs may be unconnected to the proximal ends of the plurality of second legs.

In a further exemplary embodiment, a medical device includes an elongate member defining a lumen and a basket retractable within and extendable from the lumen. The basket includes a plurality of proximal legs extending from a proximal end of the basket and a plurality of distal legs extending to a distal end of the basket. Each of the plurality of proximal legs is connected to an end of at least two of the plurality of distal legs between the proximal and distal ends of the basket. The plurality of distal legs form a knot at the distal end of the basket.

In embodiments, the plurality of distal legs may comprise a plurality of first legs and a plurality of second legs. A portion of at least one leg of the plurality of first and second legs may be coated with a protective material. The basket may have a partially expanded position in which at least a portion of the plurality of proximal legs is disposed within the lumen of the elongate member, and a distal end of each of the plurality of first legs extends distal a proximal end of each of the plurality of first legs. In addition, the basket may have a substantially circular shape in an expanded position. At least one leg of the plurality of first and second legs may extend in a direction substantially perpendicular to a longitudinal axis of the basket when the basket is in an expanded position. In addition, the proximal ends of the plurality of first legs may be connected, the proximal ends of the plurality of second legs may be connected, and the proximal ends of the plurality of first legs may be unconnected to the proximal ends of the plurality of second legs.

In still another exemplary embodiment of the present disclosure, a medical device includes an elongate member defining a lumen and a basket. The basket is retractable within and extendable from the lumen. The basket has a proximal end and a distal end and includes a plurality of proximal legs extending from the proximal end of the basket and a plurality of separate distal legs extending to the distal end of the basket. Each of the plurality of proximal legs is connected to an end of at least two of the plurality of separate distal legs between the proximal and distal ends of the basket. The basket has a partially expanded position in which at least a portion of the plurality of proximal legs is disposed within the lumen of the elongate member, and a midsection of each of the plurality of separate distal legs extends distal each end of each of the plurality of separate distal legs.

Moreover, The plurality of proximal legs may be formed from a single piece of material and the elongate member may comprise a metal coated with a polymer. Each leg of the plurality of separate distal legs may extend between distal ends of two legs of the plurality of proximal legs. The basket may have a substantially circular shape in an expanded position. In addition, at least one leg of the plurality of separate distal legs may extend in a direction substantially perpendicular to a longitudinal axis of the basket when the basket is in an expanded position. A portion of at least one leg of the plurality of separate distal legs may be coated with a protective material.

In yet another exemplary embodiment of the present disclosure, a medical device includes an elongate member defining a lumen and a basket retractable within and extendable from the lumen. The basket includes a pair of proximal legs and a plurality of separate wires. Each wire of the plurality of separate wires extends between distal ends of the pair of proximal legs.

In addition, the pair of proximal legs is formed from a single piece of material and the elongate member comprises a metal coated with a polymer. The basket may have a partially expanded position in which at least a portion of the pair of proximal legs is disposed within the lumen of the elongate member, and a midsection of each of the plurality of separate wires extends distal each end of each of the plurality of separate wires. The basket may have a substantially circular shape in an expanded position. Moreover, at least one wire of the plurality of separate wires may extend in a direction substantially perpendicular to a longitudinal axis of the basket when the basket is in an expanded position. A portion of at least one wire of the plurality of separate wires is coated with a protective material.

In a further exemplary embodiment, a method of removing a stone from the body of a patient includes providing a medical device according to one of the above embodiments. The method further includes advancing the medical device to a treatment site within the body of the patient, capturing the stone within the basket of the device, removing the medical device from the body of the patient.

An exemplary method may also include immobilizing the stone with the plurality of proximal legs of the basket, reducing the size of the stone, and advancing a laser fiber to the treatment site to assist in reducing the size of the stone. The method may further include preventing particles of the stone from escaping from the treatment site with the plurality of separate distal legs of the basket and may include sweeping at least a portion of the stone from the treatment site with the plurality of separate distal legs of the basket.

In a further exemplary embodiment of the present disclosure, a method of removing a stone from the body of a patient includes providing a medical device having an elongate member defining a lumen and a basket retractable within and extendable from the lumen. The basket includes a pair of proximal legs and a plurality of separate wires. Each wire of the plurality of separate wires extends between distal ends of the pair of proximal legs. The method further includes advancing the medical device to a treatment site within the body of the patient, capturing the stone within the basket of the device, and removing the medical device from the body of the patient.

An exemplary method may also include immobilizing the stone with the pair of proximal legs of the basket, reducing the size of the stone, and advancing a laser fiber to the treatment site to assist in reducing the size of the stone. An exemplary method may further include preventing particles of the stone from escaping from the treatment site with the plurality of separate wires of the basket and may also include sweeping at least a portion of the stone from the treatment site with the plurality of separate wires of the basket.

It is to be understood that both the foregoing general description and the following detailed description are exemplary and explanatory only, and are not restrictive of the invention as claimed.

DETAILED DESCRIPTION

Exemplary embodiments of the present disclosure are illustrated in the accompanying drawings. Wherever possible, the same reference numbers will be used throughout the drawings to refer to the same or like parts.

Figure 1:
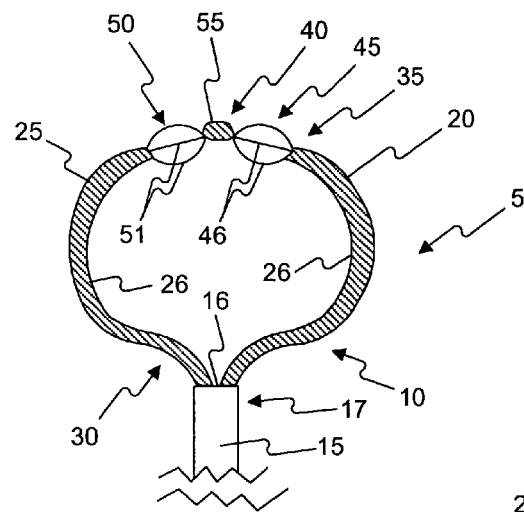
FIG. 1 illustrates a stone retrieval device according to an embodiment of the present disclosure.

FIG. 1 illustrates a stone retrieval device 5 according to an embodiment of the present disclosure. The device 5 includes a basket 10 and an elongate member 15. As will be described, basket 10 extends from and retracts within a distal end of elongate member 15. The basket 10 includes a first leg 20, a second leg 25, and a multi-wire distal section 40 having a tip 55. The basket 10 has a proximal end 30 and a distal end 35. In addition, at least one of the legs 20, 25 of the basket 10 may have an inward facing surface 26 that is textured.

As shown in FIG. 1, the elongate member 15 may be a sheath of the type known in the art. The elongate member 15 may be formed from, for example, a rod, tube, hypotube, cannula, stent, or other piece of substantially hollow cylindrical material. Alternatively, the elongate member 15 may be formed from a flat sheet of material. If formed from a flat sheet, the elongate member 15 may be formed into a substantially cylindrical shape.

The elongate member 15 may be composed of any biocompatible material or any combination of biocompatible materials known in the art. Such materials may include, but are not limited to, polyamide, PEBAX, stainless steel (such as 300 and 400 series), cobalt chromium, nickel, titanium, nitinol, thermoforming plastic, polytetrafluoroethylene ("PTFE"), and expanded polytetrafluoroethylene ("ePTFE"). The elongate member 15 may also be a metal coated with a polymer and may have one or more layers of material. The elongate member 15 may have the same or different flexibility characteristics along its length.

The elongate member 15 may include at least one open channel 16 therein. The open channel 16 may provide a passage within which other medical devices such as, but not limited to, laser fibers (not shown) may travel. The open channel 16 may also provide a passage which the basket 10 may extend from and retract into. The channel 16 may further provide a passage through which fluid may be delivered to or removed from a treatment site, such as a location of a targeted stone within the body. It is understood that the elongate member 15 may include separate open channels (not shown) for each medical device, apparatus, or other structure or fluid delivered to or removed from the treatment site.

The overall length and diameter of the elongate member 15 may vary depending on the application. For example, a relatively long elongate member 15 may be advantageous for retrieving stones or other calculi deep within the body of the patient. In addition, an elongate member 15 having a relatively small diameter may be advantageous for retrieving stones from restricted passageways within the human urinary tract. The elongate member 15 may be relatively flexible to facilitate the retrieval of stones located in complex body structures.

As mentioned above, the basket 10 of the device 5 may include a first leg 20 and a second leg 25. The first and second legs 20, 25 may extend through at least a portion of the elongate member 15 and may enter and exit the distal end 17 of the elongate member 15 through the open channel 16. The proximal ends of first and second legs 20, 25 may be operatively connected to an elongate actuator (not shown) within elongate member 15 to allow for relative movement of one or both of the elongate member 15 and the elongate actuator with respect to each other. The elongate actuator may be a flexible wire, cable, or other like structure. The elongate actuator and the elongate member 15 may connect to a proximal handle (not shown) for relative movement of the elongate actuator and member 15. Such relative movement may cause all or a portion of basket 10 to extend from or retract within member 15, and may cause basket 10 to open and close.

The first and second legs 20, 25 of the basket 10 may be formed by, for example, laser cutting, chemical etching, die cutting, or mechanically slicing a single piece of material. Alternatively, the first and second legs 20, 25 may be two separate pieces of material such as, but not limited to, separate wires. If separate, the first and second legs 20, 25 may be bonded, welded, soldered or otherwise attached together, and/or to the elongate actuator extending proximally therefrom, by any conventional means known in the art.

The desired width and length of the first and second legs 20, 25 may vary depending on the particular application, and each of the legs 20, 25 may have the same or different lengths and widths. Although FIG. 1 shows a basket 10 having only a first and second leg 20, 25, other embodiments of the basket 10 may include additional legs to facilitate the retrieval of a stone.

The first and second legs 20, 25 may be composed of, for example, nitinol, stainless steel, or other shape memory alloys known in the art. The legs 20, 25 may be, for example, cylindrical, flat, square, semi-circular, arced, D-shaped, rectangular, or ovular in shape, and may have any other cross-sectional shape known in the art. In one embodiment, each of the first and second legs 20, 25 may have a cross-sectional area equal to at least 0.015 in×0.003 in. The first and second legs 20, 25 may be in the range of approximately 0.25 in to approximately 1.0 in long, and may be long enough to hold a stone having a dimension larger than approximately 3 mm. The first and second legs 20, 25 may thus form a basket 10 having a diameter in the range of approximately 4 mm to approximately 15 mm.

The legs 20, 25 may be cold worked or heat processed to form a shape in memory. The shape may be fully formed when the elongate member 15 is retracted and the basket is allowed to fully expand. Alternatively, the shape may be partially formed when the elongate member 15 is partially retracted. The resulting basket 10 may be any shape useful in capturing and/or retrieving a stone.

Although not shown, it is understood that at least a portion of at least one of the legs 20, 25 of the basket 10 may be coated with, for example, a layer of PTFE, ePTFE, polyvinylethylene, or other material to protect the first and second legs 20, 25 during processes such as, for example, laser lithotripsy. It is also understood that the size, shape, and cross-sectional area of the first and second legs 20, 25 may provide additional protection during these processes.

In addition, at least a portion of at least one of the first and second legs 20, 25 may include an inward facing surface 26 textured to improve the stone retrieval capabilities of the device 5, and may include, for example, indentations, teeth, spikes, treads, serrations, or other structures known in the art. The texture of the inward facing surface 26 may provide multi-point contact with the stone and may be pointed away from sensitive tissue within the body structure so as not to cause trauma thereto.

As FIG. 1 illustrates, the first and second legs 20, 25 attach to multi-wire distal section 40 at the distal end 35 of the basket 10. The distal section 40 may have a first portion 45 and a second portion 50, and may include a tip 55 disposed therebetween. The first and second portions 45, 50 may include a plurality of legs 46, 51 respectively. Legs 46, 51 may be formed out of the same piece of material as the first and second legs 20, 25 respectively. Thus, the legs 46, 51 may be formed by, for example, laser cutting, chemical etching, die cutting, or mechanically slicing at least a portion of the first and second legs 20, 25. Alternatively, each of the legs 46, 51 may be formed out of separate pieces of material, such as individual wires. Each of the legs 46, 51 may thus be bonded, welded, soldered, or attached to the respective legs 20, 25 of the basket 10. If the legs 46, 51 are so formed, each of the legs 46, 51 may be composed of the same or different materials, and may thus have the same or different mechanical properties.

Although FIG. 1 illustrates three legs 46 and three legs 51, the first and second portions 45, 50 may have any number of legs 46, 51 helpful in capturing and immobilizing a stone. The desired widths and lengths of legs 46, 51 may vary depending on the particular application, and each of the legs 46, 51 may have the same or different lengths and widths. For example, legs 46, 51 may be in the range of approximately 0.25 in to approximately 0.5 in long.

Legs 46, 51 may be any cross-sectional shape known in the art including, but not limited to, cylindrical, flat, square, semi-circular, arced, D-shaped, rectangular, or ovular. Legs 46, 51 may also be coated with the same or similar materials as those described above with respect to the first and second legs 20, 25 of the basket 10 to protect the legs 46, 51 during, for example, laser lithotripsy.

As shown in FIG. 1, an end of each of the legs 46, 51 may connect to the tip 55. The tip 55 may be sized and shaped to assist in the capture and retrieval of stones within the body. For example, the tip 55 may be blunt, rounded, flat, smooth, knotted, or any other atraumatic shape known in the art. It may be as small as possible so as not to interfere with the capture and retrieval of the targeted stone, and in some embodiments of the present disclosure (discussed in greater detail below), the device 5 may not have a tip 55. Tip 55 may be composed of the same material as the legs 46, 51, and the tip 55 may be formed by soldering, welding, cementing, or otherwise connecting the ends of the legs 46, 51 together.

Alternatively, the tip 55 may be formed by tying the legs 46, 51 together into a knot or other shape. In such an embodiment, legs 46, 51 may not be separate pieces of material, but instead each leg 46 and the corresponding leg 51, may be a single piece of material. For example, an embodiment of the present disclosure may have a distal section 40 that includes three separate pieces of material. The three pieces of material may be tied together to form three legs 46, and three legs 51. The three legs 46 may be attached to a first leg 20 and the three legs 51 may be attached to a second leg 25.

Figure 2:
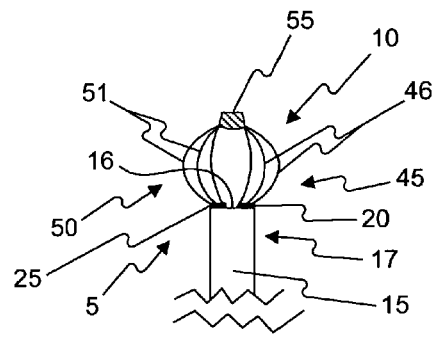
FIG. 2 illustrates an alternate configuration of the device of FIG. 1.

FIG. 2 illustrates an additional configuration of the device 5 of FIG. 1. In this configuration, at least a portion of the first and second legs 20, 25 of the basket 10 may be housed within the elongate member 15. As previously discussed, the first and second legs 20, 25 may enter and exit the distal end 17 of the elongate member 15 through the open channel 16. Thus, in this configuration, legs 46, 51 form the retrieval basket 10 of the device 5. Legs 46, 51 may come together at the tip 55 and may be sized to enable the capture of a stone less than approximately 3 mm long along its longest dimension. In all embodiments and configurations of the present disclosure, the lengths of the first and second legs 20, 25 and of legs 46, 51 may be altered to accommodate different stone size ranges or specific sized stones.

Figure 3:
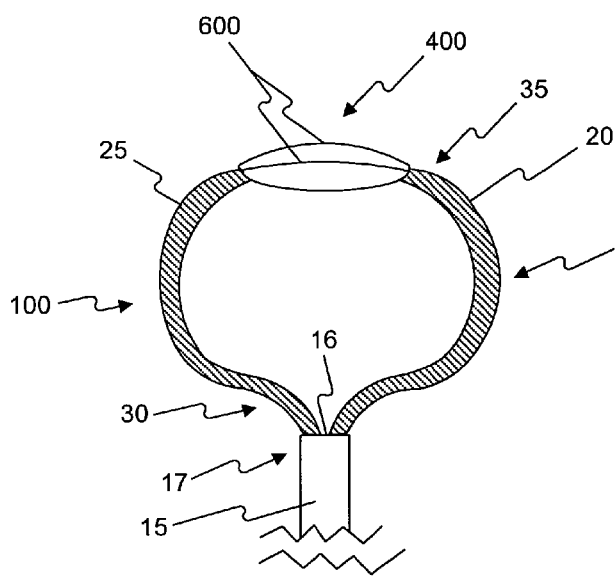
FIG. 3 illustrates a stone retrieval device according to another embodiment of the present disclosure.

FIG. 3 illustrates another embodiment of the present disclosure. In this embodiment, the device 100 includes a basket 10 and an elongate member 15. The basket 10 further includes a first leg 20, a second leg 25, and a multi-wire distal section 400 having a plurality of legs 600. The device 100 may have similar structural features as the device 5 described above with the exception of the distal section 400 as compared to distal section 40 of device 5. Distal section 400 includes one set of legs 600 without a tip 55.

Figure 4:
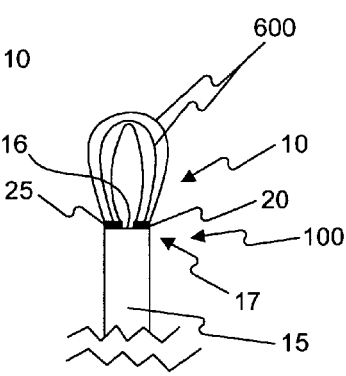
FIG. 4 illustrates an alternate configuration of the device of FIG. 3.

FIG. 4 shows another configuration of the device 100 of FIG. 3 in which at least a portion of the first and second legs 20, 25 are housed within the elongate member 15. Thus, the legs 600 form the basket 10 of the device 100 and may be sized to enable the capture of a stone less than approximately 3 mm long along its longest dimension. The legs 600 may further include a flexibility feature (not shown) or other stress relief feature to assist in forming the basket 10 when at least a portion of the first and second legs 20, 25 are within the elongate member 15.

At least some aspects of the present disclosure may be used, for example, to retrieve stones, calculi, or other material from any location within the body, such as, for example, in the urinary tract of the patient. The device 5, 100 may be inserted through the urethra of the patient, or alternatively, the device 5, 100 may be inserted percutaneously.

Although not shown, the stone targeted for retrieval may be a kidney stone, a struvite, a uric acid stone, a cystine stone, or other solid deposit commonly removed from a body structure or passageway within the body. Such stones may contain various combinations of chemicals including, but not limited to, calcium, oxalate, and phosphate. The stone may be of any size, and could have a length or diameter of approximately 1 mm to 12 mm. It is understood that these lengths and diameters are merely exemplary and that aspects of the present disclosure may assist in the retrieval of stones larger or smaller than those discussed herein. It is further understood that stones may be of any shape, and could be, for example, flat, round, smooth, or jagged. It is still further understood that the device 5, 100 may retrieve stones that are both impacted and free floating.

The device 5, 100 may be advanced to a treatment site within the body over a guidewire passing through all or a part of the open channel 16. As mentioned above, the treatment site may correspond to the location of a targeted stone. The device 5, 100 may also be advanced through an access sheath, stent, or other access or dilatation device known in the art. In addition, the device 5, 100 may be used in conjunction with an endoscope (not shown), or other type of intracorporeal scope known in the art. The endoscope may advance through the body over a guidewire to the treatment site. Alternatively, the endoscope may be independently fed to the treatment site without the use of a guidewire. Once the treatment site has been reached, the device 5, 100 may be fed through an access port of the endoscope to gain access to the stone.

While being advanced to the treatment site, the basket 10 of the device 5, 100 may be at least partially, and preferably fully, enclosed within the elongate member 15. This configuration (not shown) may minimize the size of the device 5, 100 and may assist in advancing the device 5, 100 through the endoscope. Upon exiting the endoscope and accessing the stone, the user may extend at least a portion of the basket 10 from the distal end 17 of the elongate member 15. The basket 10 may then be manipulated relative to the stone so as to capture the stone within the basket 10. Once captured, the stone may be retrieved by removing the device 5, 100 from the body of the patient.

The user may alter the configuration of the device 5, 100 based on the size of the targeted stone. The device 5, 100 of the present disclosure may achieve any number of different configurations corresponding to the position of the first and second legs 20, 25 and legs 46, 51, 600 of the basket 10 relative to the elongate member 15.

For example, if the targeted stone is larger than approximately 3 mm, the stone may be too large to be safely removed from the body. In these situations, the user may use a device configuration in which the first and second legs 20, 25 are at least partially extended from the distal end 17 of the elongate member 15, for example the basket 10 is approximately half to fully opened. Such a configuration may aid in immobilizing the stone, both holding the stone and acting as a backstop, during stone reduction processes. The half to fully opened basket 10 may prevent particles of the stone from migrating or escaping from the treatment site during or after a laser fiber (not shown) or other device acts to break up the stone. The first and second legs 20, 25 may hold the stone stationary and distal section 40, 400, including legs 46, 51, 600, may act as a backstop.

The first and second legs 20, 25 may also provide a wide opening at the proximal end 30 of the basket 10 to allow for the entrance of the laser fiber. The laser fiber may be fed to the stone through an open channel 16 of the device 5, 100. Alternatively, the laser fiber may be fed through an access port of an endoscope, external to the device 5, 100, while the device 5, 100 is disposed within the same or a different endoscope. The laser fiber may be activated and controlled by the user to reduce the size of the stone or to fragment it into smaller pieces. A proximal end of the laser fiber may connect to a power source (not shown). Once the stone has been reduced, the device 5, 100 may act as a sweeping device to sweep out of the body, stones and stone particles obtained from the reduction process. The user may employ a different device configuration, such as that shown in FIG. 2, to facilitate the sweeping of these smaller stones or particles.

If the stone is smaller than approximately 3 mm, the stone may be removed safely from the body without risk of injury, and may not require the use of stone reduction processes. In these situations, the user may employ a device configuration in which the first and second legs 20, 25 are at least partially retracted within the elongate member 15, for example completely within member 15 to about half-way extended from the distal end of member 15. In this configuration, the legs 46, 51, 600 may form the basket 10. To remove the stone, the device 5, 100 may be positioned in the vicinity of the targeted stone and the basket 10 may be partially opened. The stone may be captured within the basket 10 and may be removed by collapsing the basket 10 about the stone and removing the device 5, 100 from the body of the patient.

The device 5, 100 may also enable the user to release a stone. The user may wish to release the stone if, for example, the user encounters a restriction in the body while sweeping the stone through the urinary tract. Such a restriction might include, but is not limited to, swelling, scar tissue, or other stones or foreign matter. The restriction may be sized or positioned so as to impede the stone's progress through the urinary tract, thereby necessitating releasing the stone from the device 5, 100.

To release the stone, the elongate member 15 may be at least partially retracted allowing the basket 10 to expand. Expanding the basket 10 may discontinue contact between the stone and the first and second legs 20, 25 or legs 46, 51, 600 and may release the stone. Once the stone is released, the user may reduce the size of the stone using any of the methods discussed above. It is understood that the stone may be released in this manner regardless of the embodiment or the configuration of the device 5, 100 employed by the user.

Other embodiments of the invention will be apparent to those skilled in the art from consideration of the specification and practice of the invention disclosed herein. For example, the device 5, 100 may include a handle operatively attached to a proximal end of the elongate member 15. The handle may be capable of manipulating at least the first and second legs 20, 25 of the basket 10. In addition, foam, mesh, webbing, or some other material may be attached to a number of the legs 46, 51, 600 to assist in the capture, retrieval or immobilization of a stone. It is intended that the specification and examples be considered as exemplary only, with the true scope and spirit of the invention being indicated by the following claims.

What is claimed is:

1. A medical device, comprising:
an elongate member defining a lumen; and
a tipless basket having a proximal end and a distal end, the basket being retractable within and extendable from the lumen, the basket including a plurality of proximal legs extending from the proximal end of the basket and a plurality of distal legs extending to the distal end of the basket, each of the plurality of proximal legs being connected to an end of at least two of the plurality of distal legs between the proximal and distal ends of the basket such that the plurality of distal legs are not directly attached to any material of the medical device other than the proximal legs, the basket including a distalmost end consisting of the plurality of distal legs, each individual distal leg being separated from, not meeting, and not crossing each other when extended from the lumen, wherein the plurality of proximal legs and the plurality of distal legs are a continuous piece of a single material, wherein each of the plurality of distal legs is thinner than the rest of the continuous piece of the single material, wherein, in a first position when the basket is at least partially withdrawn into the lumen, the ends of one of the plurality of distal legs are closer together than in a second position when the basket is at least partially extended from the lumen.

2. The medical device of claim 1, wherein the elongate member comprises a metal coated with a polymer.

3. The medical device of claim 1, wherein the basket has a partially expanded position in which at least a portion of the plurality of proximal legs is disposed within the lumen of the elongate member, and a midsection of each of the plurality of distal legs extends distal each end of each of the plurality of distal legs.

4. The medical device of claim 1, wherein each leg of the plurality of distal legs extends between distal ends of two legs of the plurality of proximal legs.

5. The medical device of claim 1, wherein the basket has a substantially circular shape in an expanded position.

6. The medical device of claim 1, wherein at least one leg of the plurality of distal legs extends in a direction substantially perpendicular to a longitudinal axis of the basket when the basket is in an expanded position.

7. The medical device of claim 1, wherein a portion of at least one leg of the plurality of distal legs is coated with a protective material.

8. The medical device of claim 1, wherein all of the plurality of distal legs are separated from each other when extended from the lumen.

9. The medical device of claim 1, wherein the plurality of proximal legs include a first shape when withdrawn into the lumen and a second shape different from the first shape when external the lumen.

10. The medical device of claim 1, wherein each distal leg includes a first end and a second end, one of the plurality of proximal legs being connected to the first ends of at least two distal legs, and another of the plurality of proximal legs being connected to the second ends of the at least two distal legs.

11. A medical device, comprising:
an elongate member defining a lumen; and
a basket having a proximal end and a distal end, the basket being retractable within and extendable from the lumen, the basket including a plurality of proximal legs extending from the proximal end of the basket and a plurality of distal legs extending to the distal end of the basket each of the plurality of distal legs including a first end, a second end, and a midsection between the first and second ends, each of the plurality of proximal legs being connected to one of the first end and the second end of at least two of the plurality of distal legs between the proximal and distal ends of the basket, the basket including a distalmost end consisting of the plurality of distal legs, each individual distal leg being separated from, not meeting, and not crossing each other when extended from the lumen, the basket having a partially expanded position in which at least a portion of the plurality of proximal legs is disposed within the lumen of the elongate member, and the midsection of each of the plurality of distal legs extends distal each of the first end and the second end of each of the plurality of distal legs, wherein the plurality of proximal legs and the plurality of distal legs are a continuous piece of a single material, wherein each of the plurality of distal legs is thinner along its entire length than the rest of the continuous piece of the single material, wherein, in a first position when the basket is at least partially withdrawn into the lumen, the first and second ends of one of the plurality of distal legs are closer together than in a second position when the basket is at least partially extended from the lumen, and wherein at least one leg of the plurality of distal legs extends in a direction substantially perpendicular to a longitudinal axis of the basket when the basket is in an expanded position.

12. The medical device of claim 11, wherein the elongate member comprises a metal coated with a polymer.

13. The medical device of claim 11, wherein each leg of the plurality of distal legs extends between distal ends of two legs of the plurality of proximal legs.

14. The medical device of claim 11, wherein a portion of at least one leg of the plurality of distal legs is coated with a protective material.

15. The medical device of claim 11, wherein all of the plurality of distal legs are separated from each other when extended from the lumen.

16. The medical device of claim 11, wherein the basket is tipless.

17. A medical device, comprising:
an elongate member defining a lumen; and
a basket having a proximal end and a distal end, the basket being retractable within and extendable from the lumen, the basket including a plurality of proximal legs extending from the proximal end of the basket and a plurality of distal legs extending to the distal end of the basket each of the plurality of distal legs including a first end, a second end, and a midsection between the first and second ends, each of the plurality of proximal legs being connected to one of the first end and the second end of at least two of the plurality of distal legs between the proximal and distal ends of the basket, the basket including a distalmost end consisting of the plurality of distal legs, each individual distal leg being separated from, not meeting, and not crossing each other when extended from the lumen, the basket having a partially expanded position in which at least a portion of the plurality of proximal legs is disposed within the lumen of the elongate member, and the midsection of each of the plurality of distal legs extends distal each end of each of the plurality of distal legs, wherein the plurality of proximal legs and the plurality of distal legs are a continuous piece of a single material, wherein each of the plurality of distal legs is thinner along its entire length than the rest of the continuous piece of the single material, wherein, in a first position when the basket is at least partially withdrawn into the lumen, the ends of one of the plurality of distal legs are closer together than in a second position when the basket is at least partially extended from the lumen, and wherein the basket has a substantially circular shape in an expanded position.

18. A medical device, comprising:
an elongate member defining a lumen; and
a basket retractable within and extendable from the lumen, the basket including a pair of proximal legs, each of the pair of proximal legs being connected to one of a first end and a second end of a plurality of wires, each wire of the plurality of wires extending between distal ends of the pair of proximal legs, the basket including a distalmost end consisting of the plurality of wires, each individual wire being separated from, not meeting, and not crossing each other when extended from the lumen, wherein the plurality of wires and the pair of proximal legs are a continuous piece of a single material, wherein each of the plurality of wires is thinner than the rest of the continuous piece of the single material, wherein, in a first position when the basket is at least partially withdrawn into the lumen, the first and second ends of one of the plurality of wires are closer together than in a second position when the basket is at least partially extended from the lumen, and wherein at least one wire of the plurality of wires extends from its first end to its second end in a direction substantially perpendicular to a longitudinal axis of the basket when the basket is in an expanded position.

19. The medical device of claim 18, wherein the elongate member comprises a metal coated with a polymer.

20. The medical device of claim 18, wherein the basket has a partially expanded position in which at least a portion of the pair of proximal legs is disposed within the lumen of the elongate member, and a midsection of each of the plurality of wires extends distal each end of each of the plurality of wires.

21. The medical device of claim 18, wherein the basket has a substantially circular shape in an expanded position.

22. The medical device of claim 18, wherein a portion of at least one wire of the plurality of wires is coated with a protective material.

23. The medical device of claim 18, wherein the basket is tipless.

24. A method of removing a stone from the body of a patient, comprising:
providing a medical device according to claim 1 or 11;
advancing the medical device to a treatment site within the body of the patient;
capturing the stone within the basket of the device; and
removing the medical device from the body of the patient.

25. The method of claim 24, further including immobilizing the stone with the plurality of proximal legs of the basket.

26. The method of claim 25, further including reducing the size of the stone.

27. The method of claim 26, further including advancing a laser fiber to the treatment site to assist in reducing the size of the stone.

28. The method of claim 26, further including preventing particles of the stone from escaping from the treatment site with the plurality of distal legs of the basket.

29. The method of claim 26, further including sweeping at least a portion of the stone from the treatment site with the plurality of distal legs of the basket.

30. A method of removing a stone from the body of a patient, comprising:
providing a medical device according to claim 18;
advancing the medical device to a treatment site within the body of the patient;
capturing the stone within the basket of the device; and
removing the medical device from the body of the patient.

31. The method of claim 30, further including immobilizing the stone with the pair of proximal legs of the basket.

32. The method of claim 31, further including reducing the size of the stone.

33. The method of claim 32, further including advancing a laser fiber to the treatment site to assist in reducing the size of the stone.

34. The method of claim 32, further including preventing particles of the stone from escaping from the treatment site with the plurality of wires of the basket.

35. The method of claim 32, further including sweeping at least a portion of the stone from the treatment site with the plurality of wires of the basket.

* * * * *

UNITED STATES PATENT AND TRADEMARK OFFICE
CERTIFICATE OF CORRECTION

PATENT NO. : 8,211,115 B2
APPLICATION NO. : 11/122326
DATED : July 3, 2012
INVENTOR(S) : Eric Cheng et al.

Page 1 of 1

It is certified that error appears in the above-identified patent and that said Letters Patent is hereby corrected as shown below:

Claim 11, Column 10, Line 28, insert -- , -- after "basket".

Claim 17, Column 11, Line 9, insert -- , -- after "basket".

Claim 17, Column 11, Line 23, insert -- of the first end and the second -- after "each".

Claim 17, Column 11, Line 30, insert -- first and second -- after "lumen, the".

Signed and Sealed this
Twenty-eighth Day of August, 2012

David J. Kappos
*Director of the United States Patent and Trademark Office*